(12) United States Patent
Yamamoto et al.

(10) Patent No.: US 6,833,353 B1
(45) Date of Patent: Dec. 21, 2004

(54) USE OF IMMUNOSUPPRESSANTS FOR MMP MEDIATED DISEASES

(75) Inventors: Nobuchika Yamamoto, Tsukuba (JP); Harumi Yamazaki, Ibaraki (JP); Takeshi Ishikawa, Amagasaki (JP); Shigeru Johki, Tsukuba (JP); Fumihiko Sakai, Tsukuba (JP)

(73) Assignee: Fujisawa Pharmaceutical Co., Ltd., Osaka (JP)

( * ) Notice: Subject to any disclaimer, the term of this patent is extended or adjusted under 35 U.S.C. 154(b) by 0 days.

(21) Appl. No.: 09/786,359

(22) PCT Filed: Sep. 10, 1999

(86) PCT No.: PCT/JP99/04978

§ 371 (c)(1),
(2), (4) Date: Mar. 14, 2001

(87) PCT Pub. No.: WO00/15208

PCT Pub. Date: Mar. 23, 2000

(30) Foreign Application Priority Data

Sep. 14, 1998 (AU) ............................................. PP5841

(51) Int. Cl.[7] ............................................. A61K 38/00
(52) U.S. Cl. ................................. 514/9; 514/2; 514/11; 514/886; 424/78.05
(58) Field of Search ............................... 514/2, 11, 886, 514/9, 321, 291, 263.32; 424/78.05, 434, 435, 436

(56) References Cited

U.S. PATENT DOCUMENTS 5,352,671 A    10/1994   Baumann et al.

FOREIGN PATENT DOCUMENTS

| DE | 43 29 503 | 3/1995 | |
|----|-----------|--------|---|
| WO | WO 91/17754 | 11/1991 | |
| WO | WO 93/18048 | 9/1993 | |
| WO | WO 93/18050 | 9/1993 | |
| WO | WO 98/11908 | * 3/1998 | .......... A61K/38/13 |

OTHER PUBLICATIONS

Mnder et al. 2002. Immumophilins and HIV–1 Infection, Arch. Virol., vol. 147, pp. 1531–1542.*

Gottschall, P.E., 1996, B–amyloid Induction of Gelatinase B Secretion in Cultered Microglia: Inhibition by Dexamethasone. Neuroreport 7(18):30–77–3080.*

Milad et al. 1995. Interaction of the Progesterone Receptor with Binding Proteins for FK506 and Cyclosporin A. Molecular Endocrinology 9: 838–847.*

T. Kato, Nippon Shishubyo Gakkai Kaisha, vol. 37, No. 2, pp. 211–223, "Effect of immunosuppressant Drug (FK 506 and Ciclosporin) on Gingival Fibroblasts", 1995.

M. J. Tocci, et al., The Journal of Immunology, vol. 143, No. 2, pp. 718–726, "The Immunosuppressant FK 506 Selectviely Inhibits Expression of Early T Cell Activation Genes", Jul. 15, 1989.

C. Arita, et al., Clin. Exp. Immunol., vol. 82, No. 3, pp. 456–461, "Inhibition by FK 506OF Established Lesions of Collagen–Induced Arthritis in Rats", 1990.

K. Koch, et al., Inflamation Res., vol. 44, Supplement 2, pp. S183–S184, "CP–123,369: A Potent, Orally Active Immunosuppressive Agent", 1995.

E. Sujiyama, et al., The Journal of Rheumatology, vol. 21, No. 9, pp. 1597–1601, "FK506, An Immunosuppressant, Partially Inhibits Interleukin 6 Production by Adherent Rheumatoid Synovial Cells", 1994.

R. J. Griffiths, et al., Agents Actions, vol. 36, No. 1–2, pp. 146–151, "Characterisation of Passively Transferred Antigen Arthritis Induced by Methylated Bovine Serum Albumin in the Rat: Effect of FK 506 on Arthritis Development", 1992.

A. Zeniya, et al., Journal of Gastroenterology, vol. 29, No. 3, pp. 383–384, "Anti–Ulcer Effect of FK 506, Immunosuppressive Agent, In Rats", 1994.

T. Karashima, et al., Journal of Dermatological Science, vol. 12, No. 3, pp. 246–254, "FK 506 and Cyclosporin A Inhibit Growth Factor–Stimulated Human Keratinocyte Proliferation by Blocking Cells in the G0/G1 Phases of the Cell Cycle", 1996.

U. Mrowietz, et al., British Journal of Dermatology, vol. 139, No. 6, pp. 992–996, "The Novel Ascomycin Derivative SDZ 981 is Effective for Psoriasis when used Topically Under Occlusion", 1998.

S. P. Butcher, et al., The Journal of Neuroscience, vol. 17, No. 18, pp. 6939–6946, "Neuroprotective Actions of FK506 in Experimental Stroke: In Vivo Evidence Against An Antiexcitotoxic Mechanism", Sep. 15, 1997.

(List continued on next page.)

*Primary Examiner*—Christopher Tate
*Assistant Examiner*—B. Dell Chism
(74) *Attorney, Agent, or Firm*—Leydig, Voit & Mayer, Ltd.

(57) ABSTRACT

A new use of immunosuppressant for treating or preventing MMp-medicated diseases is provided. The preferred immunosuppresants are tacrolimus, cyclosporing A or 33-epi-chloro-33-desoxyascomycin (pimecrolimus). Particularly, preferable MMP-mediated diseases are the diseases or conditions caused by gelatinase and/or collagenase, and/or inflammatory diseases concerned with gelatinase; such as arthritis (e.g., osteoarthritis, rheumatoid arthritis, etc.) cerebral diseases (e.g., stroke, etc.), tissue ulceration (e.g., corneal, epidermal and gastriculceration, etc.), abnormal wound healing, periodontal diseases, bone diseases (e.g., Paget's diseases, osteoporosis. etc.), tumor growth, tumor metastasis or invasion, HIV-infection, decubitus, decubitis ulcer, restenosis, epidermolysis bullosa, sepsis, septic shock, neoplasm, psoriasis, neovascularization and multiple sclerosis.

19 Claims, No Drawings

OTHER PUBLICATIONS

H. Inaba, et al., Sei Mariana–ika Diagaku Zasshi, vol. 26, No. 5, pp. 555–563, "Effect of Indomethacin and Tacrolimus Hydrate on the Healing Process of Experimental Gastic Ulcers of Rats Created By Mucosal Resection: Course of Changes in the Interleukin–1β (Il–1β) Expression", 1998.

W. J. Sandborn, The American Journal of Gastroenterology, vol. 92, No. 5, pp. 876–879, "Preliminary Report on the Use of Oral Tacrolimus (FK506) in the Treatment of Compli cated Proximal Small Bowel and Fistulizing Crohn's Desease", 1997.

Y. Hisanaga, et al., Alimentary Phamacology & Therapeutics, vol. 10, No. 10, pp. 933–940, "Implicaiton of Nitric Oxide Synthase Activity in the Genesis of Water Immersion Stress–Induced Gastric Lesions in Rats: The Protective Effects of FK506", 1996.

* cited by examiner

USE OF IMMUNOSUPPRESSANTS FOR MMP MEDIATED DISEASES

FIELD OF THE INVENTION

This invention relates to a new use of an immunosuppressant. More specifically, this invention relates to a new use of immunosuppressant as matrix metallproteinases production inhibitor (hereinafter, referred to as MMP-production inhibitor).

BACKGROUND ART

Matrix metalloproteinases (hereinafter, referred to as MMPs) are a large family of $Zn^{2+}$ endopeptidases that include 72 and 92 kDa gelatinase, collagenase, stromelysin and membrane-bound MMPs. They are expressed in inflammatory coditions and collectively capable of degrading most connective tissues. MMPs, such as gelatinase (MMP-2, MMP-9), stromelysin (MMP-3) and collagenase (MMP-1, MMP-8, MMP-13), are involved in tissue matrix degradation and have been implicated in many pathological conditions involving abnormal connective tissue and basement membrane matrix metabolism.

DISCLOSURE OF THE INVENTION

This invention provides a new use of an immunosuppressant as MMP-production inhibitor.

Further, this invention provide a new MMP-production inhibitor comprising an immunosuppressant as an active ingredient.

Still further, this invention provide a new use of an immunosuppressant for manufacturing a medicament for preventing or treating MMP-mediated diseases, and a new method by using its medicament and a medicament therefor.

Various immunosuppressants have already been known. For example, it is well known that cyclosporins and tacrolimus (FK506), and their derivatives, possess a strong immunosuppressive activity, which were shown in, for example, J. Antibiotics 40(1987), 1256–1265, U.S. Pat. No. 4,929,611, and so on.

The inventors of this invention have surprisingly found that the immunosuppressant mentioned herein below has a new activity, i.e., MMP-production inhibitory activity.

The "immunosuppressant" used in the present invention should not be limited.

One example of the immunosuppressant is macrolides of the following formula (I).

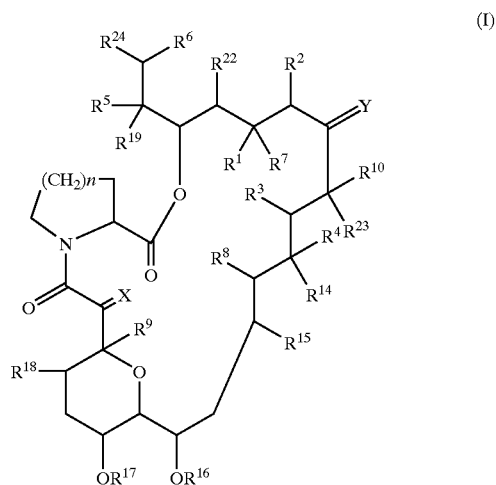

(wherein each of adjacent pairs of $R^1$ and $R^2$, $R^3$ and $R^4$, and $R^5$ and $R^6$ independently
  (a) is two adjacent hydrogen atoms, but $R^2$ may also be an alkyl group or
  (b) may form another bond formed between the carbon atoms to which they are attached;

$R^7$ is a hydrogen atom, a hydroxy group, a protected hydroxy group, or an alkoxy group, or an oxo group together with $R^1$;

$R^8$ and $R^9$ are independently a hydrogen atom or a hydroxy group;

$R^{10}$ is a hydrogen atom, an alkyl group, an alkyl group substituted by one or more hydroxy groups, an alkenyl group, an alkenyl group substituted by one or more hydroxy groups, or an alkyl group substituted by an oxo group;

X is an oxo group, (a hydrogen atom and a hydroxy group), (a hydrogen atom and a hydrogen atom), or a group represented by the formula —$CH_2O$—;

Y is an oxo group, (a hydrogen atom and a hydroxy group), (a hydrogen atom and a hydrogen atom), or a group represented by the formula N—$NR^{11}R^{12}$ or N—$OR^{13}$;

$R^{11}$ and $R^{12}$ are independently a hydrogen atom, an alkyl group, an aryl group or a tosyl group;

$R^{13}$, $R^{14}$, $R^{15}$, $R^{16}$, $R^{17}$, $R^{18}$, $R^{19}$, $R^{22}$ and $R^{23}$ are independently a hydrogen atom or an alkyl group;

$R^{24}$ is an optionally substituted ring system which may contain one or more heteroatoms;

n is an integer of 1 or 2; and in addition to the above definitions, Y, $R^{10}$ and $R^{23}$, together with the carbon atoms to which they are attached, may represent a saturated or unsaturated 5- or 6-membered nitrogen, sulfur and/or oxygen containing heterocyclic ring optionally substituted by one or more groups selected from the group consisting of an alkyl, a hydroxy, an alkoxy, a benzyl, a group of the formula —$CH_2Se(C_6H_5)$, and an alkyl substituted by one or more hydroxy groups.

Preferable $R^{24}$ may be cyclo($C_{5-7}$)alkyl group, and the following ones can be exemplified.
(a) a 3,4-di-oxo-cyclohexyl group;
(b) a 3-$R^{20}$-4-$R^{21}$-cyclohexyl group,
in which $R^{20}$ is hydroxy, an alkoxy group, an oxo group, or a —OCH$_2$OCH$_2$CH$_2$OCH$_3$ group, and
$R^{21}$ is hydroxy, —OCN, an alkoxy group, a heteroaryloxy which may be substituted by suitable substituents, a —OCH$_2$OCH$_2$CH$_2$OCH$_3$ group, a protected hydroxy group, chloro, bromo, iodo, aminooxalyloxy, an azido group, p-tolyloxythiocarbonyloxy, or $R^{25}R^{26}$CHCOO—,
in which $R^{25}$ is optionally protected hydroxy or protected amino, and
$R^{26}$ is hydrogen or methyl, or
$R^{20}$ and $R^{21}$ together form an oxygen atom in an epoxide ring; or
(c) cyclopentyl group substituted by methoxymethyl, optionally protected hydroxymethyl, acyloxymethyl
(in which the acyl moiety optionally contains either a dimethylamino group which may be quaternized, or a carboxy group which may be esterified), one or more amino and/or hydroxy groups which may be protected, or aminooxalyloxymethyl. A preferred example is a 2-formyl-cyclopentyl group.

The definitions used in the above general formula (I) and the specific and preferred examples thereof are now explained and set forth in detail.

The term "lower" means, unless otherwise indicated, a group having 1 to 6 carbon atoms.

Preferable examples of the "alkyl groups" and an alkyl moiety of the "alkoxy group" include a straight or branched chain aliphatic hydrocarbon residue, for example, a lower alkyl group such as methyl, ethyl, propyl, isopropyl, butyl, isobutyl, pentyl, neopentyl and hexyl.

Preferable examples of the "alkenyl groups" include a straight or branched chain aliphatic hydrocarbon residue having one double-bond, for example, a lower alkenyl group such as vinyl, propenyl (e.g., allyl group), butenyl, methylpropenyl, pentenyl and hexenyl.

Preferable examples of the "aryl groups" include phenyl, tolyl, xylyl, cumenyl, mesityl and naphthyl.

Preferable protective groups in the "protected hydroxy groups" and the "protected amino" are 1-(lower alkylthio)-(lower) alkyl group such as a lower alkylthiomethyl group (e.g., methylthiomethyl, ethylthiomethyl, propylthiomethyl, isopropylthiomethyl, butylthiomethyl, isobutylthiomethyl, hexylthiomethyl, etc.), more preferably $C_1$–$C_4$ alkylthiomethyl group, most preferably methylthiomethyl group;

trisubstituted silyl group such as a tri(lower)alkylsilyl (e.g., trimethylsilyl, triethylsilyl, tributylsilyl, tert-butyldimethylsilyl, tri-tert-butylsilyl, etc.) or lower alkyl-diarylsilyl (e.g., methyldiphenylsilyl, ethyldiphenylsilyl, propyldiphenylsilyl, tert-butyldiphenyl-silyl, etc.), more preferably tri($C_1$–$C_4$) alkylsilyl group and $C_1$–$C_4$ alkyldiphenylsilyl group, most preferably tert-butyldimethylsilyl group and tert-butyldiphenylsilyl group; and an acyl group such as an aliphatic, aromatic acyl group or an aliphatic acyl group substituted by an aromatic group, which are derived from a carboxylic acid, sulfonic acid or carbamic acid.

Examples of the aliphatic acyl groups include a lower alkanoyl group optionally having one or more suitable substituents such as carboxy, e.g., formyl, acetyl, propionyl, butyryl, isobutyryl, valeryl, isovaleryl, pivaloyl, hexanoyl, carboxyacetyl, carboxypropionyl, carboxybutyryl, carboxyhexanoyl, etc.;

a cyclo(lower)alkoxy(lower)alkanoyl group optionally having one or more suitable substituents such as lower alkyl, e.g., cyclopropyloxyacetyl, cyclobutyloxypropionyl, cycloheptyloxybutyryl, menthyloxyacetyl, menthyloxypropionyl, menthyloxybutyryl, menthyloxypentanoyl, menthyloxyhexanoyl, etc.; a camphorsulfonyl group; or a lower alkylcarbamoyl group having one or more suitable substituents such as carboxy or protected carboxy, for example, carboxy(lower)alkylcarbamoyl group (e.g., carboxymethylcarbamoyl, carboxyethylcarbamoyl, carboxypropylcarbamoyl, carboxybutylcarbamoyl, carboxypentylcarbamoyl, carboxyhexylcarbamoyl, etc.), tri-(lower)alkylsilyl (lower) alkoxycarbonyl (lower) alkylcarbamoyl group (e.g., trimethylsilylmethoxycarbonylethylcarbamoyl, trimethylsilylethoxycarbonylpropylcarbamoyl, triethylsilylethoxycarbonylpropylcarbamoyl, tert-butyldimethylsilylethoxycarbonylpropylcarbamoyl, tri-methylsilylpropoxycarbonylbutylcarbamoyl, etc.) and so on.

Examples of the aromatic acyl groups include an aroyl group optionally having one or more suitable substituents such as nitro, e.g., benzoyl, toluoyl, xyloyl, naphthoyl, nitrobenzoyl, dinitrobenzoyl, nitronaphthoyl, etc.; and an arenesulfonyl group optionally having one or more suitable substituents such as halogen, e.g., benzenesulfonyl, toluenesulfonyl, xylenesulfonyl, naphthalenesulfonyl, fluorobenzenesulfonyl, chlorobenzenesulfonyl, bromobenzenesulfonyl, iodobenzenesulfonyl, etc.

Examples of the aliphatic acyl groups substituted by an aromatic group include ar(lower)alkanoyl group optionally having one or more suitable substituents such as lower alkoxy or trihalo(lower)alkyl, e.g., phenylacetyl, phenylpropionyl, phenylbutyryl, 2-trifluoromethyl-2-methoxy-2-phenylacetyl, 2-ethyl-2-trifluoromethyl-2-phenylacetyl, 2-trifluoromethyl-2-propoxy-2-phenylacetyl, etc.

More preferable acyl groups among the aforesaid acyl groups are $C_1$–$C_4$ alkanoyl group optionally having carboxy, cyclo($C_5$–$C_6$)alkoxy($C_1$–$C_4$)alkanoyl group having two ($C_1$–$C_4$) alkyls at the cycloalkyl moiety, camphorsulfonyl group, carboxy-($C_1$–$C_4$)alkylcarbamoyl group, tri ($C_1$–$C_4$) alkylsilyl ($C_1$–$C_4$) alkoxycarbonyl ($C_1$–$C_4$)-alkylcarbamoyl group, benzoyl group optionally having one or two nitro groups, benzenesulfonyl group having halogen, or phenyl ($C_1$–$C_4$) alkanoyl group having $C_1$–$C_4$ alkoxy and trihalo ($C_1$–$C_4$)alkyl group. Among these, the most preferable ones are acetyl, carboxypropionyl, menthyloxyacetyl, camphorsulfonyl, benzoyl, nitrobenzoyl, dinitrobenzoyl, iodobenzenesulfonyl and 2-trifluoromethyl-2-methoxy-2-phenylacetyl.

Preferable examples of the "5- or 6-membered nitrogen, sulfur and/or oxygen containing heterocyclic ring" include a pyrrolyl group and a tetrahydrofuryl group.

"A heteroaryl which may be substituted by suitable substituents" moiety of the "heteroaryloxy which may be substituted by suitable substituents" may be the ones exemplified for $R^1$ of the compound of the formula of EP-A-532, 088, with preference given to 1-hydroxyethylindol-5-yl, the disclosure of which is incorporated herein by reference.

The compounds (I) and its pharmaceutically acceptable salt for use in accordance with this invention are well known to have excellent immunosuppressive activity, antimicrobial activity and other pharmacological activities and, as such, be of value for the treatment or prevention of rejection reactions by transplantation of organs or tissues, graft-vs-host diseases, autoimmune diseases, and infectious diseases [EP-A-0184162, EP-A-0323042, EP-A-423714, EP-A-427680, EP-A-465426, EP-A-480623, EP-A-532088, EP-A-532089, EP-A-569337, EP-A-626385, WO89/05303, WO93/05058, WO96/31514, WO91/13889, WO91/19495, WO93/5059, etc.], the disclosures of which are incorporated herein by reference.

Particularly, the compounds which are designated as FR900506 (=FK506), FR900520 (ascomycin), FR900523, and FR900525 are products produced by microorganisms of the genus Streptomyces, such as *Streptomyces tsukubaensis* No. 9993 [deposited with National Institute of Bioscience and Human Technology Agency of Industrial Science and Technology (formerly Fermentation Research Institute Agency of Industrial Science and Technology ), at 1–3, Higashi 1-chome, Tsukuba-shi, Ibaraki, Japan, date of deposit Oct. 5, 1984, accession number FERM BP-927] or *Streptomyces hygroscopicus* subsp. *yakushimaensis* No. 7238 [deposited with National Institute of Bioscience and Human Technology Agency of Industrial Science and Technology (formerly Fermentation Research Institute Agency of Industrial Science and Technology ), at 1–3, Higashi 1-chome, Tsukuba-shi, Ibaraki, Japan, date of deposit Jan. 12, 1985, accession number FERM BP-928][(EP-A-0184162]. The FK506 (general name: tacrolimus) of the following chemical formula, in particular, is a representative compound.

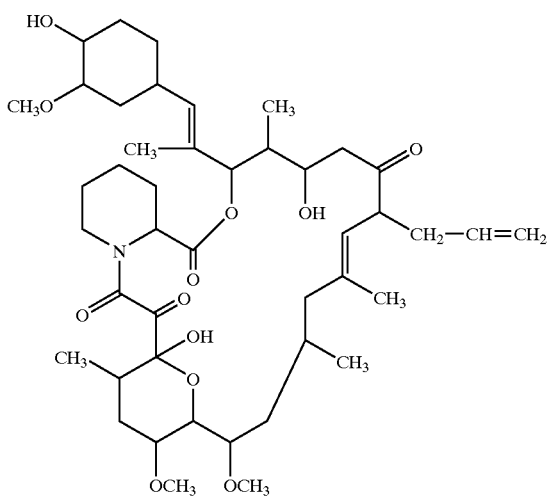

Chemical name: 17-allyl-1,14-dihydroxy-12-[2-(4-hydroxy-3-methoxycyclohexyl)-1-methylvinyl]-23,25-dimethoxy-13,19,21,27-tetramethyl-11,28-dioxa-4-azatricyclo [22.3.1.0$^{4,9}$] octacos-18-ene-2,3,10,16-tetraone The preferable macrolides (I) is tacrolimus, ascomycin or its derivatives such as 33-epi-chloro-33-desoxyascomycin, which is disclosed in EP 427,680, example 66a. Other preferable compounds (I) are, for example, the compound of example 6d in EP569337, and the compound of example 8, EP626385.

The compounds shown in EP-0184162, EP323042, EP424714, EP427680, EP465426, EP474126, EP480623, EP484936, EP532088, EP532089, EP569337, EP626385, WO89/05303, WO93/05058, WO96/31514, WO91/13889, WO91/19495, WO93/5059, WO96/31514 and so on, are also exemplified as the preferable examples of the macrolides (I), the disclosures of which are incorporated herein by reference.

Further example of the immunosuppressant is cyclosporins, such as cyclosporin A, B, D, etc, which are shown in THE MERCK INDEX (12th edition), No. 2821, the disclosure of which is incorporated herein by reference.

Still further example of the immunosuppressant is an another type of macrolide which is called as rapamycin [THE MERCK INDEX (12th edition), No. 8288] and its derivatives. Preferable example of the derivatives is an O-substituted derivative in which the hydroxy in position 40 of formula A illustrated at page 1 of WO 95/16691, incorporated herein by reference, is replaced by —OR$_1$ in which R$_1$ is hydroxyalkyl, hydroalkoxyalkyl, acylaminoalkyl and aminoalkyl; for example 40-O-(2-hydroxy)ethyl-rapamycin, 40-O-(3-hydroxy)propyl-rapamycin, 40-O-[2-(2-hydroxy) ethoxy]ethyl-rapamycin and 40-O-(2-acetaminoethyl)-rapamycin. These O-substituted derivatives may be produced by reacting rapamycin (or dihydro or deoxo-rapamycin) with an organic radical attached to a leaving group (for example RX where R is the organic radical which is desired as the O-substituent, such as an alkyl, allyl, or benzyl moiety, and X is a leaving group such as CCl$_3$C (NH)O or CF$_3$SO$_3$) under suitable reaction conditions. The conditions may be acidic or neutral conditions, for example in the presence of an acid like trifluoromethanesulfonic acid, camphorsulfonic acid, p-toluenesulfonic acid or their respective pyridinium or substituted pyridinium salts when X is CCl$_3$C(NH)O or in the presence of a base like pyridine, a substituted pyridine, diisopropylethylamine or pentamethylpiperidine when X is CF$_3$SO$_3$. The most preferable one is 40-O-(2-hydroxy)ethyl rapamycin, which is disclosed in WO94/09010, the disclosure of which is incorporated herein by reference.

The macrolides (I), and rapamycin and its derivatives, have a similar basic structure, i.e., tricyclic macrolide structure, and at least one of the biological properties (for example, immunological properties).

The preferable immunosuppressant in the present invention is the one having the inhibitory activity on TNF-α and/or IFN-γ production.

The immunosuppressant may be in a form of its salt, which includes conventional non-toxic and pharmaceutically acceptable salt such as the salt with inorganic or organic bases, specifically, an alkali metal salt such as sodium salt and potassium salt, an alkali earth metal salt such as calcium salt and magnesium salt, an ammonium salt and an amine salt such as triethylamine salt and N-benzyl-N-methylamine salt.

With respect to the immunosuppressant such as the macrolides (I), it is to be understood that there may be conformers and one or more stereoisomers such as optical and geometrical isomers due to asymmetric carbon atom(s) or double bond(s), and such conformers and isomers are also included within the scope of the present invention.

The immunosuppressant, particularly the macrolides (I) or its pharmaceutically acceptable salt, can be in the form of a solvate, which is included within the scope of the present invention. The solvate preferably include a hydrate and an ethanolate.

And further, the immunosuppressant can be in the form of pro-drugs, suitable derivatives, and so on.

The preferred examples of the immunosuppressant are the macrolides (I), wherein each of adjacent pairs of $R^3$ and $R^4$ or $R^5$ and $R^6$ independently form another bond formed between the carbon atoms to which they are attached;

each of $R^8$ and $R^{23}$ is independently a hydrogen atom;

$R^9$ is a hydroxy group;

$R^{10}$ is a methyl group, an ethyl group, a propyl group or an allyl group;

X is (a hydrogen atom and a hydrogen atom) or an oxo group;

Y is an oxo group;

each of $R^{14}$, $R^{15}$, $R^{16}$, $R^{17}$, $R^{18}$, $R^{19}$, and $R^{22}$ is a methyl group;

$R^{24}$ is a 3-$R^{20}$-4-$R^{21}$-cyclohexyl group,
  in which $R^{20}$ is hydroxy, an alkoxy group, an oxo group, or a —OCH$_2$OCH$_2$CH$_2$OCH$_3$ group, and $R^{21}$ is hydroxy, —OCN, an alkoxy group, a heteroaryloxy which may be substituted by suitable substituents, a —OCH$_2$OCH$_2$CH$_2$OCH$_3$ group, a protected hydroxy group, chloro, bromo, iodo, aminooxalyloxy, an azido group, p-tolyloxythiocarbonyloxy, or $R^{25}R^{26}$CHCOO—,
    in which $R^{25}$ is optionally protected hydroxy or protected amino, and
    $R^{26}$ is hydrogen or methyl, or
  $R^{20}$ and $R^{21}$ together form an oxygen atom in an epoxide ring; and n is an integer of 1 or 2.

Tacrolimus is the most preferable compound belonging to the immunosuppressant. Other preferable compounds are listed herein below.

17-Ethyl-1,14-dihydroxy-12- [2-(4-hydroxy-3-methoxycyclohexyl)-1-methylvinyl]-23,25-dimethoxy- 13,19,21,27-tetramethyl-11,28-dioxa-4-azatricyclo[22.3.1.0 $^{4,9}$]octacos-18-ene-2, 3,10,16-tetraone (=ascomycin): 33-epi-chloro-33-desoxyascomycin (EP-A-427680, example 66a): and 40-O-(2-hydroxy) ethyl rapamycin (WO94/0910)

"MMP-production inhibitor" in the present invention is used to mean the one having inhibitory or reducing activity on the production of MMPs. Preferable MMPs is gelatinase and collagenase. Most preferable "MMP-production inhibitor" is collagenase-production inhibitor.

"MMP-mediated diseases" in the present invention is used to mean various diseases and pathological conditions caused by MMPs involving abnormal connective tissue and basement membrane matrix metabolism.

Particularly, preferable MMP-mediated diseases are the diseases or conditions caused by gelatinase and/or collagenase, and/or inflammatory diseases concerned with gelatinase; such as arthritis (e.g., osteoarthritis, rheumatoid arthritis, etc.), cerebral diseases (e.g., stroke, etc.), tissue ulceration (e.g., corneal, epidermal and gastric ulceration, etc.), abnormal wound healing, periodontal diseases, bone diseases (e.g., Paget's diseases, osteoporosis, etc.), tumor growth, tumor metastasis or invasion, HIV-infection, decubitus, decubitis ulcer, restenosis, epidermolysis bullosa, sepsis, septic shock, neoplasm, psoriasis, neovascularization, multiple sclerosis, and soon. More preferable "MMP-mediated diseases" of the present invention is cartilage degradation and/or connective tissue degradation, and rheumatoid arthritis which accompanies such degradation.

The immunosuppressant used in the present invention may be administered as pure compounds or mixtures of compounds or preferably, in a pharmaceutical vehicle or carrier.

The pharmaceutical compositions of this invention can be used in the form of a pharmaceutical preparation, for example, in solid, semisolid or liquid form, which contains the immunosuppressant, as an active ingredient, in admixture with an organic or inorganic carrier or excipient suitable for pharmaceutical use. The active ingredient may be compounded, for example, with the usual non-toxic, pharmaceutically acceptable, carriers for solutions (saline, for example), emulsion (olive oil, for example), ointment, aerosol sprays, lotion, cream, gel, skin plasters, patches and any other form suitable for use. The carriers which can be used are water, glucose, lactose, gum acacia, gelatin, mannitol, starch paste, magnesium trisilicate, talc, cornstarch, keratin, colloidal silica, potato starch, urea and other carriers suitable for use in manufacturing preparations, in solid, semisolid, or liquid form, and in addition auxiliary, stabilizing, thickening and coloring agents and perfumes may be used. The active object compound is included in the pharmaceutical composition in an effective amount sufficient to produce the desired effect upon the process or condition of the disease.

Mammals which may be treated using the method of the present invention include livestock mammals such as cows, horses, etc., domestic animals such as dogs, cats, rats, etc. and humans.

While the dosage of therapeutically effective amount of the immunosuppressant varies from and also depends upon the age and condition of each individual patient to be treated, a daily dose of about 0.0001–1000 mg, preferably 0.001–500 mg and more preferably 0.01–100 mg. of the active ingredient is generally given for treating diseases, and an average single dose of about 0.001–0.01 mg, 0.2–0.5 mg, 1 mg, 5 mg, 10 mg, 50 mg, 100 mg, 250 mg and 500 mg is generally administered. Daily doses for chronic administration in humans will be in the range of about 0.1–0.3 mg/kg/day.

The following examples illustrate the present invention in further detail. It should be understood that those examples are not intended to limit the scope of the invention.

EXAMPLE 1

The inhibitory activity of FK506, which is a representative of immunosuppressant, on MMP-production was assayed by the following method.

Materials and Methods

Bone and excess tissue overlying the cartilage was removed under sterile conditions, in an airflow hood. The septum was washed in 70% ethanol before the cartilage was cut to a weight of 40×2mg. The cartilages were wrapped tightly in sterile cotton squares and soaked in 0.1 ml of a 10 mg/ml homogenized suspension of heat-killed *Mycobacterium tuberculosis* H37RA (Difco) in saline. Eight cartilages were stored in −20° C., these were to measure the levels of collagen in non-implanted cartilages.

Eight weeks old female Lewis rats were anaesthetized using halothane. The stomach area was shaved and swabbed with ethanol. A single cotton wrapped cartilage was inserted subcutaneously to the right side of a ventral midline incision. The wound was sealed using a skin staple, and the animal allowed to recover. The animals were orally dosed once daily with 0.5% methylcellulose as a control vehicle or FK506 on day 1 after cotton wrapped cartilages implantation. After fourteen days, the animals were killed and the implanted cartilage and the adjacent granulomatous tissue were excised. The removed bovine nasal cartilage was washed twice with PBS and assayed for hydroxyproline.

The individual cartilages were incubated at 65° C. in 1 ml of a phosphate buffered solution, pH 6.5, of papain (1 mg/ml) containing 2 mM N-acetyl-L-cystein and EDTA. The resulting digested cartilages were hydrolysed in 6M hydrochloric acid for 18 hr at 110° C. The hydrolysate was diluted 1:20 in acetate/citrate buffer before being assayed for hydroxyproline by using the Chrolamine T/p-dimethylamino-benzaldehyde reaction.

The granulomatous tissues were homogenized in 1 ml of 50 mM Tris, pH 7.5 containing 5 mM $CaCl_2$, 0.1% Triton X-100 and 0.02% $NaN_3$) After centrifugation of the extract at 15000 rpm for 10 min to remove debris, the supernatant was assayed for collagenolytic activity, gelatinolytic activity, tumor necrosis factor-$\alpha$ (TNF-$\alpha$) level and Interferon-$\gamma$ (IFN-$\gamma$) level. Collagenolytic and gelatinolytic activities in the extracts were measured using commercial assay kits (YAGAI, Japan). Cytokines levels were also measured using ELISA kits (Cosmo Bio, Japan). The protein contents in the extracts was determined using the method of Lowry.

Data is expressed as mean±SEM. The significance of differences was determined by Dunnett's multiple comparison test (*$p<0.05$, **$p<0.01$).

Results

FK506 was administered at a dosages of 1.0 to 3.2 mg/kg (po, uid). FK506 (3.2 mg/kg) inhibited the decrease of hydroxyproline contents in cartilage by 62% (Table 1), which indicates that cartilage degradation was decreased by the administration of FK506. As shown in Table 2, FK506 inhibited the production of collagenase and gelatinase in a dose-dependent manner.

The obtained result indicates that the immunosuppressant, such as FK506, is useful for MMP-production inhibitor, collagenase-production inhibitor, gelatinase-production inhibitor, and/or for treating or preventing MMP-mediated diseases.

It is also apparent that FK506 inhibited the elevation of TNF-$\alpha$ and IFN-$\gamma$ production in vivo (Table 3).

TABLE 1

Effect of FK506 on cartilage degradation in implant model.

| Dose (mg/kg) | Recovery (%) of Hydroxyproline |
|---|---|
| 3.2 | 61.9** |

TABLE 2

Effect of FK506 on production of MMPs in implant model.

| | inhibition (%) | |
|---|---|---|
| Dose (mg/kg) | collagenase | gelatinase |
| 1.0 | 7.7 | 67.9* |
| 3.2 | 29.8 | 82.1** |

TABLE 3

Effect of FK506 on elevation of TNF-$\alpha$ and IFN-$\gamma$ production in implant model.

| | inhibition (%) | |
|---|---|---|
| Dose (mg/kg) | TNF-$\alpha$ | IFN-$\gamma$ |
| 1.0 | 43.9** | 58.1 |
| 3.2 | 56.6** | 73.4* |

EXAMPLE 2

The following pharmaceutical composition can be applied to patients suffering MMP-medicated diseases.

| (1) Oral composition | |
|---|---|
| FK 506 Substance | 1 g |
| Hydroxypropyl methylcellulose 2910 (TC-5R) | 1 g |
| Lactose | 2 g |
| Croscarmellose sodium (Ac-Di-Sol) | 1 g |

The above composition is prepared according to a similar manner to that of EP-A-0240773.

| (2) Ointment | |
|---|---|
| FK506 Substance | 0.1 g |
| propylene carbonate | 5.00 g |
| liquid paraffin | 11.0 g |
| solid paraffin | 3.0 g |
| white bees wax | 3.5 g |
| white petrolatum | q.s. (to 100.0 g) |

The ointment composed of the above ingredient was prepared according to a similar manner to that of the Example 1 described in U.S. Pat. No. 5,385,907.

(3) Similar ointment is prepared by using 33-epi-chloro-33-desoxyascomycin, as an active ingredient, according to a similar manner to that of the above (2).

(4) Similar ointment is prepared by using 40-O-(2-hydroxy) ethylrapamycin, as an active ingredient, according to a similar manner to that of the above (2).

The patents, patent applications and publications cited herein are incorporated by reference.

What is claimed is:

1. A method of inhibiting matrix metalloprotease production in a cell in need thereof, comprising administering to said cell an effective concentration of one or more macrolides of the following formula (I):

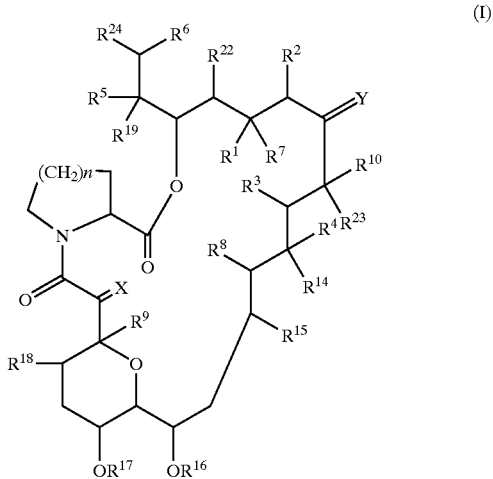

wherein each of adjacent pairs of $R^1$ and $R^2$, $R^3$ and $R^4$, and $R^5$ and $R^6$ are independently
(a) two adjacent hydrogen atoms, where $R^2$ may be an alkyl group, or
(b) form a bond so that the carbon atoms to which they are attached have a double bond therebetween;
$R^7$ is a hydrogen atom, a hydroxy group, a protected hydroxyl group, or an alkoxy group, or an oxo group together with $R^1$;
$R^8$ and $R^9$ are independently a hydrogen atom or a hydroxy group;
$R^{10}$ is a hydrogen atom, an alkyl group, an alkyl group substituted by one or more hydroxy groups, an alkenyl group, an alkenyl group substituted by one or more hydroxy groups, or an alkyl group substituted by an oxo group;
X is an oxo group, a hydrogen atom and a hydroxy group, a hydrogen atom and a hydrogen atom, or a group represented by the formula —CH$_2$O—;
Y is an oxo group, a hydrogen atom and a hydroxy group, a hydrogen atom and a hydrogen atom, or a group represented by the formula N—NR$^{11}$R$^{12}$ or N—OR$^{13}$;
$R^{11}$ and $R^{12}$ are independently a hydrogen atom, an alkyl group, an aryl group or a tosyl group;
$R^{13}$, $R^{14}$, $R^{15}$, $R^{16}$, $R^{17}$, $R^{18}$, $R^{19}$, $R^{22}$ and $R^{23}$ are independently a hydrogen atom or an alkyl group;
$R^{24}$ is an optionally substituted ring system that may contain one or more heteroatoms;
n is an integer of 1 or 2; and
wherein Y, $R^{10}$ and $R^{23}$, together with the carbon atoms to which they are attached, may represent a saturated or unsaturated 5- or 6-membered nitrogen, sulfur and/or oxygen containing heterocyclic ring optionally substituted by one or more groups selected from the group consisting of an alkyl, a hydroxy, an alkoxy, a benzyl, a group of the formula —CH$_2$Se(C$_6$H$_5$), and an alkyl substituted by one or more hydroxy groups, or a pharmaceutically acceptable salt thereof.

2. The method of claim 1, wherein said macrolides are admixed with one or more carriers or excipients.

3. The method of claim 1, wherein $R^{24}$ is a cyclo(C$_{5-7}$) alkyl group.

4. The method of claim 3, wherein said cyclo(C$_{5-7}$)alkyl group is selected from the group consisting of
a) a 3,4-di-oxo-cyclohexyl group;
b) a 3-R$^{20}$-4-R$^{21}$-cyclohexyl group,
wherein $R^{20}$ is hydroxy, an alkyoxy group, an oxo group, or a —OCH$_2$OCH$_2$CH$_2$OCH$_3$ group and $R^{21}$ is a hydroxy, —OCN, an alkoxy group, a heteroaryloxy which may be substituted by a suitable substituent, a —OCH$_2$OCH$_2$CH$_2$OCH$_3$ group, a protected hydroxyl group, chloro, bromo, iodo, amninooxyalyloxy, an azido group, p-tolyloxythiocarbonyloxy, or R$^{25}$R$^{26}$CHCOO—, wherein $R^{25}$ is a hydroxy, a protected hydroxy, an amino, a protected amino, and $R^{26}$ is hydrogen or methyl, or $R^{20}$ and $R^{21}$ together form an oxygen atom in an epoxide ring; and
c) cyclopentyl group substituted by methoxymethyl, hydroxymethyl, protected hydroxymethyl, acyloxymethyl, a acyloxymethyl in which the acyl moiety contains a dimethylamiro group which may be quaternized, or a carboxy group which may be esterified, an amino group, a protected amino group, a hydroxy group, a protected hydroxy group, and a aminooxyalyloxymethyl.

5. The method of claim 1, wherein said macrolide of formula (I) is selected from the group consisting of tacrolimus, ascomycin, and 33-epi-chloro-33-desoxyascomycin.

6. The method of claim 1, wherein said pharmaceutically acceptable salt thereof is selected from an alkali metal salt, an alkali earth metal salt, an ammonium salt, an amine salt, a hydrate, and an ethanolate.

7. The method of claim 1, wherein said effective concentration is 0.0001 to 1000 mg per day.

8. A method or treating a matrix metalloprotease-mediated disease comprising administering to a patient in need thereof an effective amount of one or more macrolides of the following formula (I):

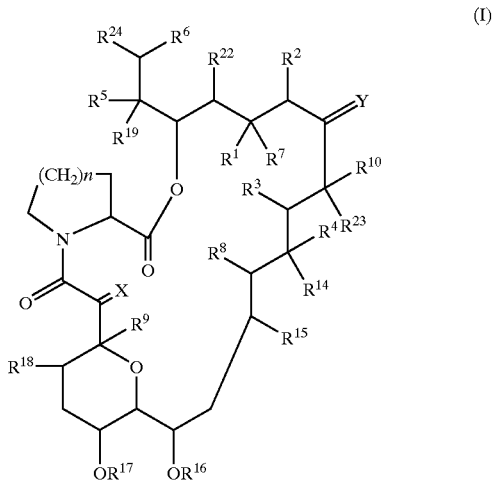

wherein each of adjacent pairs of $R^1$ and $R^2$, $R^3$ and $R^4$, and $R^5$ and $R^6$ are independently
(a) two adjacent hydrogen atoms, where $R^2$ may be an alkyl group, or (b) form a bond so that the carbon atoms to which they are attached have a double bond therebetween;

$R^7$ is a hydrogen atom, a hydroxy group, a protected hydroxyl group, or an alkoxy group, or an oxo group together with $R^1$;

$R^8$ and $R^9$ are independently a hydrogen atom or a hydroxy group;

$R^{10}$ is a hydrogen atom, an alkyl group, an alkyl group substituted by one or more hydroxy groups, an alkenyl group, an alkenyl group substituted by one or more hydroxy groups, or an alkyl group substituted by an oxo group;

X is an oxo group, a hydrogen atom and a hydroxy group, a hydrogen atom and a hydrogen atom, or a group represented by the formula —CH$_2$O—;

Y is an oxo group, a hydrogen atom and a hydroxy group, a hydrogen atom and a hydrogen atom, or a group represented by the formula N—NR$^{11}$R$^{12}$ or N—OR$^{13}$;

$R^{11}$ and $R^{12}$ are independently a hydrogen atom, an alkyl group, an aryl group or a tosyl group;

$R^{13}$, $R^{14}$, $R^{15}$, $R^{16}$, $R^{17}$, $R^{18}$, $R^{19}$, $R^{22}$ and $R^{23}$ are independently a hydrogen alkyl group;

$R^{24}$ is an optionally substituted ring system that may contain one or more heteroatoms;

n is an integer of 1 or 2; and wherein Y, $R^{10}$ and $R^{23}$, together with the carbon atoms to which they are attached, may represent a saturated or unsaturated 5- or 6-membered nitrogen, sulfur and/or oxygen containing heterocyclic ring optionally substituted by one or more groups selected from the group consisting of an alkyl, a hydroxy, an alkoxy, a benzyl, a group of the formula —CH$_2$Se(C$_6$H$_5$), and an alkyl substituted by one or more hydroxy groups, or a pharmaceutically acceptable salt thereof.

9. The method of claim 8, wherein said macrolides are admixed with one or more carriers or excipients.

10. The method of claim 8, wherein $R^{24}$ is a cyclo(C$_{5-7}$) alkyl group.

11. The method of claim 10, wherein said cyclo(C$_{5-7}$)alkyl group is selected from the group consisting of a) a 3,4-di-oxo-cyclohexyl group;

b) a 3-R$^{20}$-4-R$^{21}$-cyclohexyl group, wherein R$^{20}$ is a hydroxy, an alkyoxy group, an oxo group, or a —OCH$_2$OCH$_2$CH$_2$OCH$_3$ group, and R$^{21}$ is a hydroxy, —OCN, an alkoxy group, a heteroaryloxy which may be substituted by a suitable substituent, a —OCH$_2$OCH$_2$CH$_2$OCH$_3$ group, a protected hydroxyl group, chloro, bromo, iodo, aminooxyalyloxy, an azido group, p-tolyloxythiocarbonyloxy, or R$^{25}$R$^{26}$CHCOO—, wherein R$^{25}$ is a hydroxy, a protected hydroxy, an amino, a protected amino, and R$^{26}$ is hydrogen or methyl, or R$^{20}$ and R$^{21}$ together form an oxygen atom in an epoxide ring; and c) cyclopentyl group substituted by methoxymethyl, hydroxymethyl, protected hydroxymethyl, acyloxymethyl, a acyloxymethyl in which the acyl moiety contains a dimethyl amino group which may be quaternized, or a carboxy group which may be esterified, an amino group, a protected amino group, a hydroxy group, a protected hydroxy group, and a aminooxyalyloxymethyl.

12. The method of claim 8, wherein said macrolide of formula (I) is selected from the group consisting of tacrolimus, ascomycin, and 33-epi-chloro-33-desoxyascomycin.

13. The method of claim 8, wherein said pharmaceutically acceptable salt thereof is selected from an alkali metal salt, an alkali earth metal salt, an ammonium salt, an amine salt, a hydrate, and an ethanolate.

14. The method of claim 8, wherein said effective amount is 0.0001 to 1000 mg per day.

15. The method of claim 8, wherein said effective amount is 0.1 to 0.3 mg per kg per day.

16. The method of claim 8, wherein said matrix metalloprotease-mediated disease is one or more diseases selected from the group consisting of cartilage degradation, connective tissue degradation, rheumatoid arthritis, cerebral disease, tissue ulceration, abnormal wound healing, periodontal disease, bone disease, tumor growth, tumor metastasis, tumor invasion, decubitus, decubitus ulcer, restenosis, epidermolysis bullosa, sepsis, septic shock, neoplasm psoriasis, neovascularization, multiple sclerosis.

17. The method of claim 16, wherein said matrix metalloprotease-mediated disease is selected from the group consisting of cartilage degradation, connective tissue degradation, and rheumatoid arthritis.

18. The method of claim 8, wherein said patient in need thereof is a mammal.

19. The method of claim 18, wherein said mammal is selected from the group consisting of cows, horses, dogs, cats, rats, and humans.

* * * * *